(12) United States Patent
Wirth et al.

(10) Patent No.: US 11,717,217 B2
(45) Date of Patent: Aug. 8, 2023

(54) STRESS MONITOR AND STRESS-MONITORING METHOD

(71) Applicant: Steffen Wirth, Munich (DE)

(72) Inventors: Steffen Wirth, Munich (DE); Bernd Hälbig, Bobingen (DE); Tina Schlereth, Erding (DE)

(73) Assignee: Steffen Wirth, Munich (DE)

( * ) Notice: Subject to any disclaimer, the term of this patent is extended or adjusted under 35 U.S.C. 154(b) by 421 days.

(21) Appl. No.: 16/829,130

(22) Filed: Mar. 25, 2020

(65) Prior Publication Data

US 2020/0305791 A1    Oct. 1, 2020

(30) Foreign Application Priority Data

Mar. 25, 2019   (EP) .................................... 19164972

(51) Int. Cl.
*A61B 5/00* (2006.01)

(52) U.S. Cl.
CPC .......... *A61B 5/4884* (2013.01); *A61B 5/7264* (2013.01); *A61B 5/749* (2013.01); *A61B 2560/0431* (2013.01); *A61B 2562/02* (2013.01)

(58) Field of Classification Search
CPC ..... A61B 5/4884; A61B 5/7264; A61B 5/749; A61B 2560/0431; A61B 2562/02; A61B 5/72–5/7296; G06N 3/0454; G06N 3/08; G06N 3/0445; G16H 50/00–50/80; G06K 9/00496–0057

See application file for complete search history.

(56) References Cited

U.S. PATENT DOCUMENTS

| | | | |
|---|---|---|---|
| 10,159,411 B2* | 12/2018 | Tzvieli | A61B 5/0077 |
| 2014/0316220 A1* | 10/2014 | Sheldon | A61B 5/0205 |
| | | | 600/301 |
| 2015/0265211 A1* | 9/2015 | Schneider | A61B 5/4812 |
| | | | 600/301 |
| 2018/0116528 A1* | 5/2018 | Tzvieli | A61B 5/7264 |
| 2020/0090049 A1* | 3/2020 | Aliper | G06V 20/69 |

* cited by examiner

*Primary Examiner* — Jonathan T Kuo

(74) *Attorney, Agent, or Firm* — Browdy and Neimark, PLLC

(57) ABSTRACT

A computer-implemented method for indicating a long-term stress level of a person by means of a data processing unit, including the steps of acquiring stressor data having a set of stressor data items; analyzing stressor data values of the stressor data items by means of an artificial neural network to generate data representing a stress level, wherein the artificial neural network (ANN) is trained to provide output representing the stress level based on the stressor data values and an indication of previous stress state; and signaling the stress level.

22 Claims, 4 Drawing Sheets

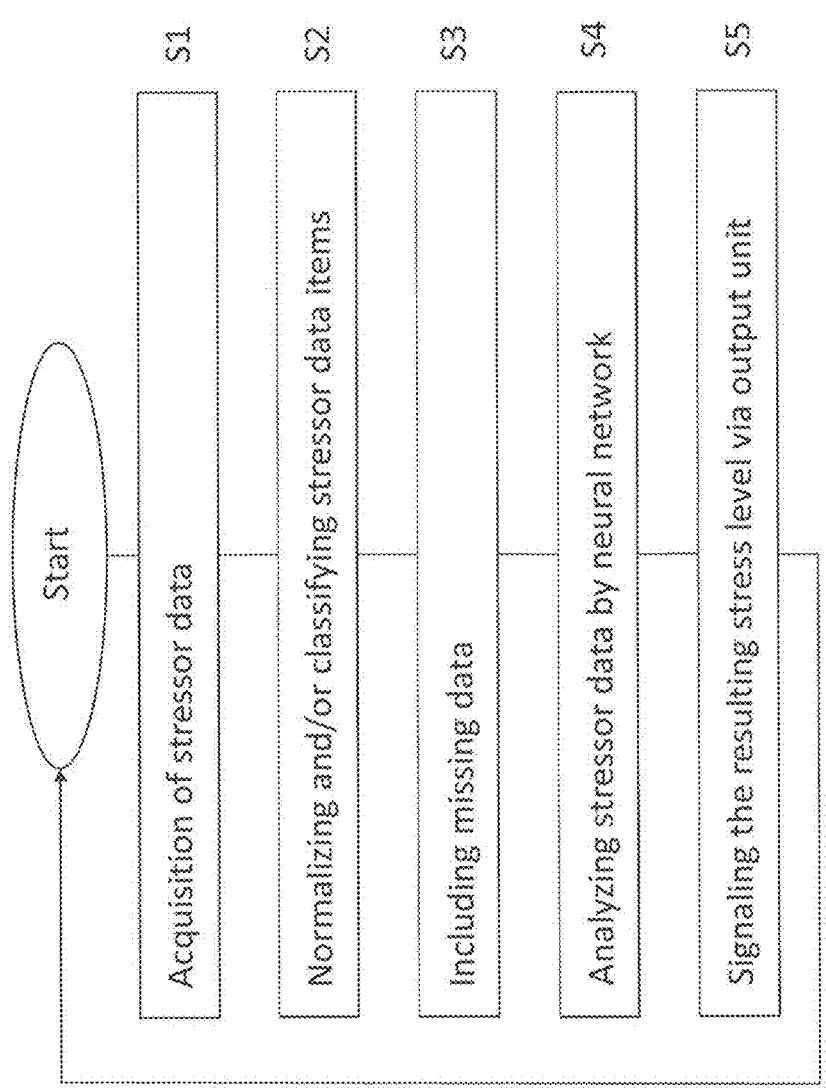

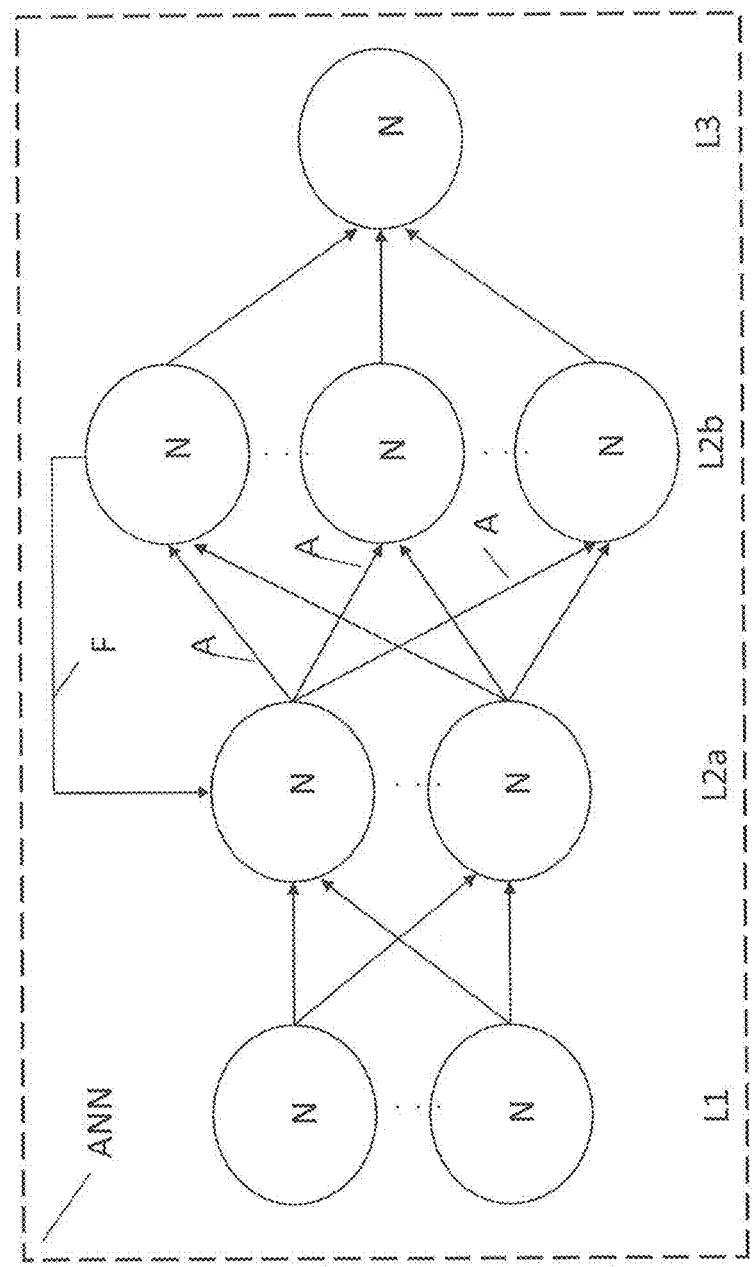

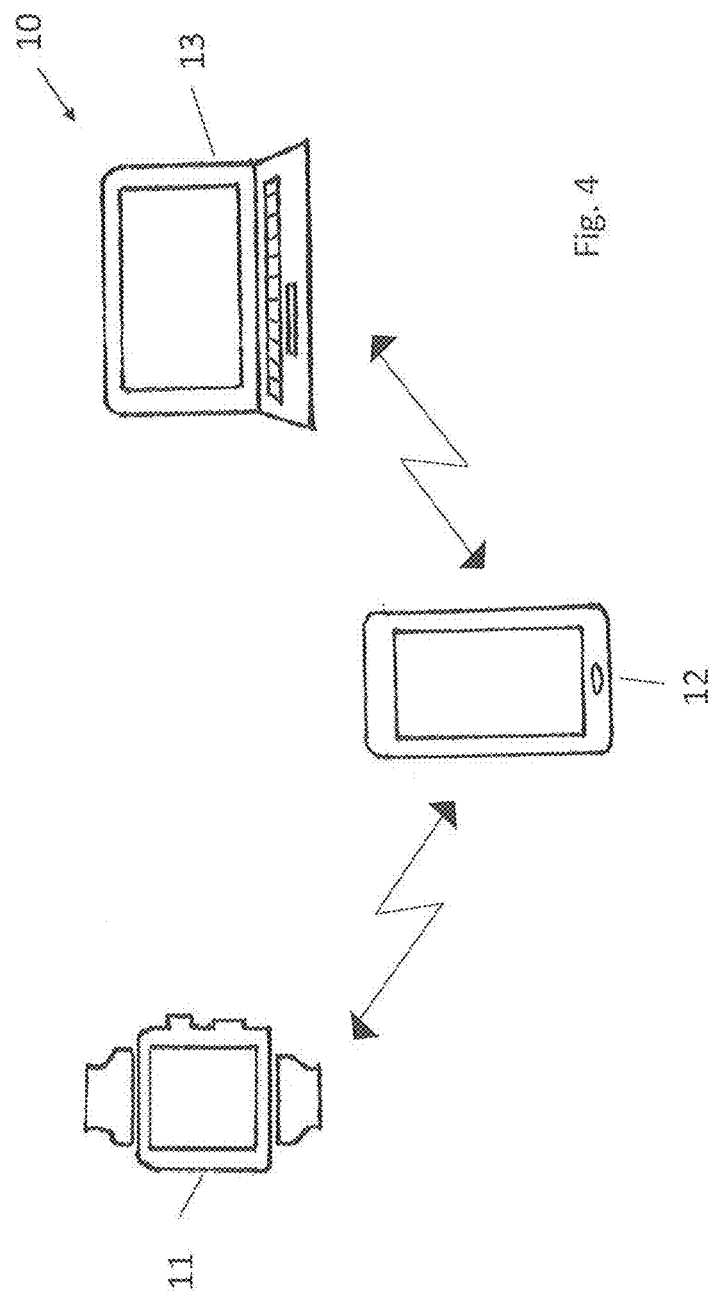

STRESS MONITOR AND STRESS-MONITORING METHOD

TECHNICAL FIELD

The present invention is related to devices for monitoring and analyzing a stress level of a person over time using a novel computer-implemented artificial neural network (ANN). Furthermore, the present invention is related to measures for providing an indicator of a stress level.

TECHNICAL BACKGROUND

Human stress is generally considered to represent a physiologic, biochemical or neuroendocrine response to an external or internal stimulus or expectation. Factors which causes stress or an increase of stress are commonly referred to as stressors. Depending on the origin of the stressor it is distinguished between external stressors and internal stressors.

There are various kinds of stressors to which a person is continuously exposed, which may be classified as sensory stressors caused by impact of external stimuli, social stressors caused by interaction with other person, groups or machines and emotional stressors caused by unfulfilled expectations, fears and the like. Particularly, internal (emotional) stressors are hardly to anticipate, but which substantially add to the effects of the exposure of external stressors. Furthermore, the impact of each stressor on a person's homeostasis does not merely add, but can also amplify effects of other stressors to have an essential impact on the stress level of the person.

While sudden incidences may affect a short-termed increase of a stress level, also a long-term impact on the stress level can be observed, particularly when those incidences frequently occur. The long-termed stress level is considered as an important factor in conjunction with symptoms like the burnout syndrome, which essentially results from long-term unresolvable stress. Burn-out syndrome substantially affects a person's life and his ability to perform tasks and take over responsibilities in job and private life. In addition, stress substantially affect creativity and the person's ability to think innovatively, which is also reflected in the sustainability of higher-level teams, organizations and companies.

The process of the development of a burnout syndrome is slow, so that the relevance of monitoring long-termed stress may help to recognize and assess the risks for having a burnout of a person and to take preventive action against it at an early stage.

From document WO 2010/107788 A2, it is known a stress monitoring method which includes the steps of acquiring a plurality of individual readings of at least one physiologic data parameter over a period of time, storing the plurality of individual readings, determining the average of at least a portion of the plurality of individual readings, and comparing at least one individual reading to the average to identify any differences between the average and the at least one individual reading.

Furthermore, from document US 2012/0289790 A1 it is known a method includes accessing data streams from a mood sensor and one or more of a heart-rate monitors, a blood-pressure monitor, a pulse oximeter, or an accelerometer monitoring a person, analyzing data sets collected from the person when the person is stressed and unstressed, analyzing the data sets, and determining a current stress index of the person based on the analysis.

In US 2009/0069641 A1, it is disclosed a method and system for analyzing stress and managing stress by using a mobile electronic apparatus and a data management server. The method includes: generating bio-signal pattern information upon periodically receiving a bio-signal from a bio-signal measuring device connected to each of a plurality of unspecified individuals, and forming reference information for stress analysis based on received answers to each of a plurality of questions for checking a stress level; receiving bio-signal pattern information from a bio-signal measuring device connected to a specified user; and determining a stress level corresponding to the bio-signal pattern information of the specified user based on the reference information.

SUMMARY OF THE INVENTION

According to the present invention, a computer-implemented method for using an artificial neural network (ANN) to generate output indicating a long-term stress level of a person according to claim 1 and a long-term stress-indicator device according to the further independent claim are provided.

Further embodiments are indicated in the dependent sub claims.

According to a first aspect a method for indicating a long-term stress level of a person by means of a data processing unit (e.g., a computer) is provided, comprising the steps of:
- using the data processing unit to acquire actual stressor data having a set of actual stressor data items, such as by automatically acquiring the stressor data using one or more sensors;
- using the data processing unit to analyze stressor data values of the stressor data items by means of an artificial neural network (ANN) to generate data representing a stress level, wherein the ANN is trained to provide output representing the stress level based on the stressor data values and an indication of a previous stress state; and
- using the data processing unit to signal the stress level, particularly via an output device.

One idea of the present invention is to provide a stress-monitoring method which allows to analyze various data about stressors to which a person is exposed without the need for completeness of data. This has been achieved by the stress-monitoring method using an input unit providing a variety of actual stressor data from various sources, external input or the like. Furthermore, an artificial neural network unit is used which has been trained by available data of various persons who have developed a burnout syndrome.

In general, the development of a burnout syndrome can relate on various factors. The dominant factors for the development of the burnout case may vary from case to case so that an evaluation what amount of which stressor(s) may definitely lead to a burnout, cannot be clearly made. The use of an artificial neural network to provide an appropriate model for this multi-input has the benefit that a normalization of the assessment of the stress level can be made with the reference being the accumulated stressor exposure which have led to a burnout syndrome. This basically allows to define a stress level scale with a clearly defined maximum value. This solves the general problem to find a clear reference for a stress level.

The term "stress lever" shall express herein an assessed niveau of a physical and/or psychic reaction of a person caused by exposure to external factors/stressors. The stress level may be numerically indicated and serves to express the degree of a person's physical and/or psychic reactions to ongoing impact of stressors.

The output of the artificial neural network is a stress level indicator for the long-termed stress level of the person which allows to apply anti-stress measures or stress-reducing measures to reduce the person's risk to develop a burnout syndrome. Above method has the advantage that various data about persons having developed a burnout syndrome can be accumulated and considered in a common stress level evaluating model using artificial intelligence. As the available stressor data for each of the recorded burnout cases are of a different kind and of different quality, the artificial neural network unit can also be trained when data is missing.

Furthermore, the artificial neural network may be formed as a recurrent artificial neural network, so that an output of an intermediate layer or an output layer (indication of the previous stress state) is considered via a feedback path to an input layer or to an intermediate layer of the recurrent neural network.

The evaluation may be carried out during time instances according to a given time frame, such as 3 hours and 48 hours, preferably of 24 hours.

It may be provided that missing values of one or more stressor data items are generated by a given estimation, a maximum, a minimum or an average of the previous values of the respective stressor data item over the current time frame or one or more preceding time frames.

According to an embodiment missing values of one or more stressor data items are generated by means of a data imputation method, particularly using an autoencoder.

Moreover, one or more stressor data items may be classified or normalized before being analyzed in the neural network.

Moreover, future stress levels may be predicted by extrapolating stressor data values of any stressor data item and by recurrently evaluating the stress level for succeeding time instances beginning with the current time instance at least partly based on the extrapolated stressor data values for the corresponding past time instances. The evaluation is made as before, i.e. by analyzing stressor data values of the stressor data items by means of the artificial neural network to generate data representing the stress level. Particularly, extrapolating may include a linear extrapolation or assuming a constant stressor data value for one or more of the stressor data items.

Furthermore, extrapolating may include a linear extrapolation or assuming a constant stressor data value for one or more of the stressor data items.

It may be provided that one or more stressor data items are classified or normalized before being analyzed in the artificial neural network.

The artificial neural network may comprise at least one of a deep artificial neural network, a convolutional neural network, a long-short term memory, and a classification model.

Moreover, the stressor data may be at least partly automatically acquired using one or more sensors.

It may be provided that the stressor data is at least partly acquired by retrieving input from a user.

Furthermore, the neural network may be a deep neural network or a convolutional neural network.

According to a further aspect a processing device for indicating a long-term stress level of a person by means of a data processing unit is provided, comprising:

receiving means, such as one or more sensors or one or more mobile devices, for receiving stressor data having a set of stressor data items;

a neural network trained for providing the stress level based on the stressor data values and an indication of previous stress state analyzing stressor data values of the stressor data items to obtain a stress level, wherein the neural network is trained to; and an output unit or communication unit configured to signal the stress level.

According to a further aspect, a system comprising the above processing device and a portable output device is provided, wherein the communication unit is configured to transmit an indication about the stress level to the portable output device.

BRIEF DESCRIPTION OF THE DRAWINGS

Embodiments are described in more detail in conjunction with the accompanying drawings, in which

FIG. 2 shows a flow chart for illustrating the method for monitoring a stress level.

FIG. 3 shows an example if a recurrent artificial neural network as an example for use in the stress-monitoring system;

FIG. 4 shows a schematic illustration of a distributed system for performing the stress-monitoring method according to the present invention.

DESCRIPTION OF EMBODIMENTS

Figure 1:
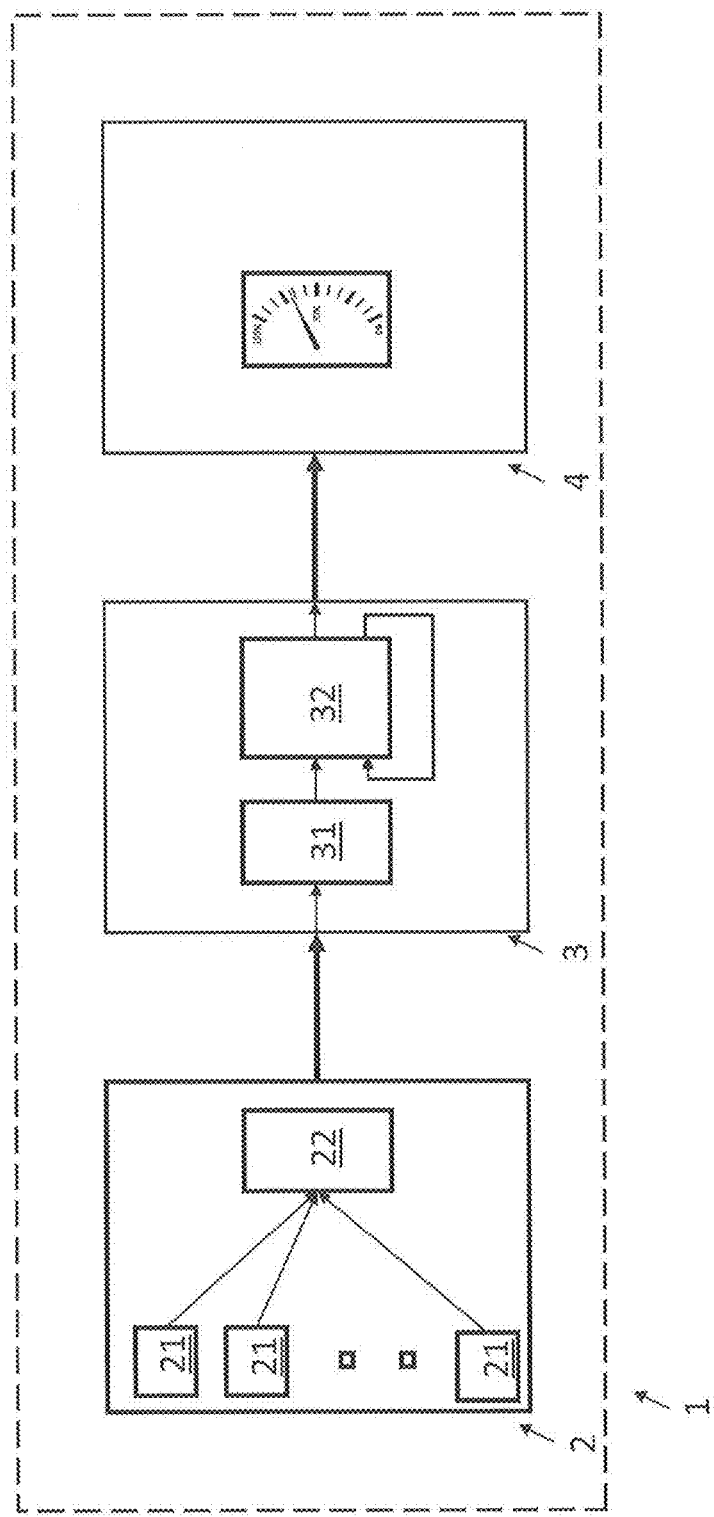
FIG. 1 shows a basic diagram for a stress-monitoring system.

In the following, a stress-monitoring system 1 is described in detail which allows to signalize a long-termed stress level of a person based on individual stressor data. The system 1 performs a method for evaluating and indicating a stress level of a person which is illustrated in the flowchart of FIG. 2.

The stress-monitoring system 1 is schematically shown in FIG. 1. The stress-monitoring system 1 includes a stressor data input unit 2 which is configured to receive, to detect or to provide stressor data related to a person's physiological condition, data, behavior, symptoms and exposure to external influences. The obtained stressor data is provided to an analyzing unit 3 which analyzes the stressor data and calculates stress level data which indicates the long-termed stress level of the person.

The long-termed stress level is signalized to an output unit 4, which provides interaction with the person or any other person or entity depending on the signalized stress level data.

The stress-monitoring system 1 may be implemented as software executed in any kind of computing device which can be a cloud computing device, a personal desktop computer or the like. Also, the stress-monitoring system 1 can be executed in a mobile device via App such as a smartphone, smartwatch or the like.

The stressor data input unit 2 is shown in detail in the block diagram of FIG. 1. The stressor data input unit 2 is configured to collect any kind of stressor data to provide them to the artificial neural network unit 3. The stressor data input unit 2 may be implemented by one or more devices which may include a personal desktop computer, a mobile device, a wearable, sensors or the like to acquire data related to symptoms and/or physiological data and the like. The stressor data input unit 2 may include one or more sensors for automatically detecting and generating and receiving signals representing stressor data. The acquisition of stressor data is performed in step S1. For instance, the stressor data input unit 2 may include stressor data acquiring units 21 such as:

- a computer terminal for inputting symptom data, such as headache (strength, time and duration), and physiological data, such as heart rate, blood pressure, heart rate variability, concentration of stress-inducing hormones (such as cortisol) in body liquids, such as blood and the like,
- a query device for querying the person about their mental state, such as stressed, happy, unhappy, relaxed, exhausted and the like and for providing corresponding mental state data,
- an activity-monitoring device, including one or more sensors for automatically detecting and generating and receiving signals representing any kind of activity of the person, such as sports, movement, sleeping times, times in specific situations, such as travel times or times talking on the phone, such as times in public transportation, travel times, television times, online times (times spend with using internet based services, such as browsing, email, messaging etc.) and the like, and for providing corresponding activity data;
- personality-type input device for inputting, e.g. via personal desktop computer, personality type data about the personality type, such as pioneer, driver, guardian, integrator, extroverted, introverted, attention as well as personal data, such as weight, age, sex, race, and the like;
- an exposure input device which is configured to query for nutrition data, medication data, drinking data, drug consumption, exposure to UV radiation and the like, and to provide body exposure data. For instance, the noise level can be continuously detected, e.g. by means of a mobile device. Thereby, a noise level and noise exposure characteristics can be detected and used as an input. Moreover, the noise characteristics can be compressed in the stressor data input unit 2 to reduce the amount of data. Furthermore, nutrition data can be relying on the characteristics of consumption of nutrition, the kind of nutrition, the amount of specific food, the time of consumption and/or the nutrient content contained therein. Moreover, medication data for medication which affects the stress level of a person may be collected and considered.
- information exposure unit which is configured to collect information exposure data about the usage of digital media, such as social media, email communication, telephone usage, usage of a smartphone for different kind of purposes and the like. Information exposure data can be input manually via a computer terminal or can be automatically sampled by software tools implemented in the person's own electronic devices, such as in his smartphone, his personal computer and the like. Relevant information exposure data may include frequency, time and duration of work-related browsing on electronic devices and/or frequency and time of email receptions on electronic devices.
- a voice-analyzing unit which may be implemented in a portable device carried by the person which is configured to detect the voice of the person (e.g., using a microphone to generate a signal representing the voice of the person) and to analyze the voice of the person (e.g., the signal representing the voice of the person) with known methods with respect to stress indicators and to provide voice stress data.
- a resilience input device to query, e.g. via a computer terminal, about the physical resilience of the person which can be received by querying with an interrogation form and the like. The resilience may be indicated by a resilience measure generated by analyzing the interrogation form.
- an environmental input device configured to automatically receive input and generate output representing environment data about the environment which may have an impact on the person's physical condition, including weather data, general news data including news about the political situation, social situations and the like and an assessment thereof.
- a financial input device configured to query about the financial situation of the person by having access to a financial database of the user.
- a group data acquisition device configured to provide stress related data of a group the person belongs to. As stress factors and the resulting physiological conditions of group members give an indication about the impact of stressors on the group such data can be considered. For instance, an indicator about stress level of other group members can be considered. Such an indicator can e.g. form an average stress level calculated from weighted stress levels of other group members. The weight factor expresses a group interrelation of the person with other group members.

In step S2, all so obtained data may be classified and/or normalized in a data classifier 22 to classify inputs in categories or into predefined value ranges. Moreover, each of the so obtained classified stressor data is provided with a time stamp associated to the point of time which the input of occurrence of the stressor was made.

A time frame, such as 6 hours, 12 hours, a day, a few days, a week, or the like is predetermined in which stressor data is supplied to the analyzing unit 3. Other time bases can be selected as well. The time frame defines a time base by which the data is analyzed so that the stress level may be adapted with respect to the time basis. The time frame indicates the time instance when an evaluation is carried out.

Each of the stressor data items may be acquired and collected once, automatically at predetermined time instances, or automatically regularly in continuous time frames. So, the stressor data items reflect the current situation at different times and in different frequencies. If the acquisition frequency of any newly acquired stressor data item is higher than that of the time frame, a plurality of time variable stressor data values is available within the time frame and the data classifier 22 may be further configured to condense data to provide a relevant stressor data item for forwarding to the analyzing unit 3. Condensing data may be made by providing the maximum, the minimum or the average or the stressor data values of the respective stressor data item within/over the time duration of the preceding time frame or a number of preceding time frames to obtain a condensed stressor data value. The condensed stressor data value is then used for evaluation at the current time instance.

If the acquisition frequency of any newly acquired stressor data item is lower than the given time frame, for each time frame the last acquired stressor data value can be used. Alternatively, the maximum, the minimum or the average or the stressor data values of the respective stressor data item within/over the time duration of a number of preceding time frames is used for evaluation. For instance, the personality type data item is used for each time frame once input is made.

The stressor data provided to the analyzing unit 3 may comprise all of the above stressor data items or only a part of the stressor data items, if some stressor data is not available.

The analyzing unit 3 comprises a missing data imputation unit 31 and an artificial neural network 32. The missing data imputation unit 31 is performed in step S3 and allows to add stressor data values for stressor data items which has not been made available by the stressor data input unit 2 or which is temporarily not available at the actual time instant.

A step S4 of analyzing stressor data in the artificial neural network 32 is performed. The artificial neural network 32 is configured to provide a stress level which can be a value in the range of 0 to 100% (0% low stress to 100% high stress) or in any other predefined fixed scale. For instance, the stress level can also be indicated as 0% for a high stress level to 100% for a low stress level.

The missing data imputation unit 31 is provided so that an incomplete set of stressor data values (no stressor data values are available for one or more stressor data items) will be completed by estimating stressor data values for unavailable stressor data items using available stressor data provided by the stressor data input unit 2. So, it may be possible to complete the set of stressor data which is required for processing within the artificial neural network 32.

For instance, missing stressor data may be given a predetermined or average value of previously acquired stressor data of the same kind. Moreover, missing stressor data can be estimated by means of a data imputation method which derives missing data from a set of known stressor data by means of e.g. an autoencoder or the like. Data imputation methods are well-known in the art and are not further described herein. As an input for the missing data imputation method, relevant stressor data is selected from the set of stressor data which have a high correlation (e.g. > between 0.8 and 0.5, or >0.75) with the missing data so that a high-quality prediction of the missing stressor data can be obtained.

The artificial neural network 32 is trained to provide a stress level output based on all stressors provided as stressor data items with respect to the given time frame. As the process of building up a stress level relevant for developing a burnout syndrome also depends on the actual situation and the actual stress level of the person, when the person is exposed to a new stressor or repeatedly exposed to a stressor, the stress level output of the artificial neural network 32 is fed back to at least one of its inputs so that depending on the actual considered stressor data the stress level is adapted, i.e. increased or decreased. This allows to consider the accumulating effect of stressors to which the person is exposed.

Following, the so obtained long term stress level may be signaled in step S5 to a local or remote output device 4 which signalizes the stress level of a person to the person or any other entity such as a medical institution. For instance, the stress level can be displayed with a graphical representation on a portable output device such as the smartphone of the person or can be automatically transmitted to the medical entity for monitoring the stress level of the person externally.

For instance, the stress level can be directly indicated as a value or on a scale. In another embodiment the stress level can be indicated reversely so that 100% indicates no stress and 0% at or close to burnout. This may be represented in the form of a fuel indicator which can be intuitively understood by the user. Moreover, the stress levels can be graphically shown in combination with colors red, yellow, green.

Furthermore, an alarm can be output such as an acoustic alarm or a visual alarm notifying the person that the stress level has reached a critical value and that stress-reducing measures should be taken immediately to avoid a serious risk of developing a burnout syndrome.

For the purpose of predicting future stress levels, the stressor data characteristics of the available stressor data items can be extrapolated. This may be done by linear extrapolation or by keeping the last obtained stressor data value of one or more stressor data items constant. Using these stressor data values, the artificial neural network 32 can be used recursively to evaluate stress level development for future time frames. Due to the non-linear model behavior implemented in the artificial neural network 32 the stress level at the future time instances has to be calculated beginning with the current time instance.

Furthermore, the artificial neural network may be formed as a recurrent artificial neural network ANN which is exemplarily shown in FIG. 3. It is schematically shown an ANN with one input layer L1, a number of succeeding intermediate layers L2a, L2b and an output layer L3 each comprising one or more neurons N as it is known in the art. The neurons N of the different layers are feed-forward coupled by axons A. The axons A are associated with weighs which represent the training of the ANN. One or more of the outputs of one of the intermediate layers L2a, L2b or of the output layer L3 (generated indication of the previous stress state) is considered via a feedback path F to the input layer L1 or to one of the preceding intermediate layers L2a, L2b of the recurrent artificial neural network. Such a configuration allows to consider the actual stress level for evaluation of a succeeding stress level of a next time frame.

As a further example, the artificial neural network may be implemented with a LSTM neural network (LSTM Long-Short Term Memory) so that the time variable stressor data can be processed to a corresponding actual stress level.

The stressor data acquiring units 21, the data imputation unit 31 and the artificial neural network 32 may each be implemented by hardware and/or software in one or more data processing systems. The data acquiring units 21 and the analyzing unit 3 can be implemented in a distributed system, wherein the analyzing unit 3 can particularly be provided as a cloud service.

The stress monitoring system 1 can be implemented as a distributed system 10 as shown in FIG. 4. The distributed system 10 may include a number of stressor data acquiring units 21 which may be formed as a wearable 11, such as a smart watch, a mobile device 12, such as a smart phone, and the like. These are interconnected with a processing device 13 which can be located at the position of the person or in a network or network cloud. The processing device 13 may comprise the data imputation unit 31 and the artificial neural network 32 so as to perform the data collection and processing of the corresponding functions. The processing device 13 may include a communication unit as a receiving means to allow wireless data communication with the wearable 11 and/or the mobile device 12 and/or other devices for acquiring stressor data.

The current stress level is communicated via the communication unit to one of the person's personal devices such as the wearable 11 or the mobile device 12 for presentation of the stress level in above mentioned manner.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention allow continuously or regularly collecting of stressor data from various sources which are operated further. Moreover, missing data imputation and artificial neural networks are complex processes which are inherently computer-implemented and which could practically not be performed manually or mentally by a human.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

The invention claimed is:

1. A computer-implemented method for indicating a long-term stress level of a person using a computer comprising a processor and a memory, the method comprising the steps of:
   acquiring stressor data having a set of stressor data items;
   analyzing stressor data values of the stressor data items by generating, using an artificial neural network, data representing a stress level, wherein the artificial neural network is trained to provide output representing the stress level based on the stressor data values and an indication of previous stress state, wherein the artificial neural network is a recurrent neural network, wherein the indication of the previous stress state is considered via a feedback path to an input of the recurrent artificial neural network to consider the accumulating effect of stressors to which the person is exposed, wherein the artificial neural network is trained by available data of various persons who have developed a burnout syndrome, wherein the burnout syndrome defines a maximum value of a stress level; and
   signaling the stress level, and
   generating missing values of one or more particular stressor data by selecting relevant stressor data from the set of stressor data which have a positive correlation with the missing data above a given correlation threshold level so that a high-quality prediction of the missing stressor data can be obtained.

2. The method according to claim 1, wherein the artificial neural network is formed as a recurrent neural network, wherein the indication of the previous stress state is considered via a feedback path to an input or to an intermediate layer of the recurrent artificial neural network, wherein the artificial neural network is implemented with a long-short term memory.

3. The method according to claim 2, wherein the evaluation is carried out in time steps or during time instances according to a given time frame.

4. The method according to claim 3, wherein the given time frame is between 3 and 48 hours.

5. The method according to claim 3, wherein the given time frame is 24 hours.

6. The method according to claim 1, further comprising generating missing values of one or more stressor data items at the time of evaluation by a given estimation, a maximum, a minimum or an average of previous values of the respective stressor data item over the current time frame or one or more preceding time frames.

7. The method according to claim 1, further comprising generating missing values of one or more stressor data items using a data imputation method using an autoencoder.

8. The method according to claim 1, further comprising predicting future stress levels by extrapolating stressor data values of any stressor data item and by recurrently evaluating the stress level for succeeding time instances beginning with the current time instance based on the extrapolated stressor data values for the corresponding time instances.

9. The method according to claim 8, wherein the extrapolating includes a linear extrapolation or assuming a constant stressor data value for one or more of the stressor data items.

10. The method according to claim 1, wherein one or more stressor data items are classified or normalized before being analyzed in the artificial neural network.

11. The method according to claim 1, wherein the artificial neural network comprises at least one of a deep artificial neural network, a convolutional neural network, long-short term memory, and classification models.

12. The method according to claim 1, wherein the stressor data is at least partly automatically acquired using one or more sensors.

13. The method according to claim 1, wherein the stressor data is at least partly acquired by retrieving input from a user.

14. The method according to claim 1, wherein acquiring stressor data having a set of stressor data items comprises using a computer terminal for querying symptom data, wherein the symptom data comprises at least one of strength, time and duration of a headache, and physiological data, wherein the physiological data comprises at least one of heart rate, blood pressure, heart rate variability, concentration of stress-inducing hormones in body liquids.

15. The method according to claim 1, wherein acquiring stressor data having a set of stressor data items comprises using a query device for querying the person about their mental state, wherein the mental state comprises at least one of stressed, happy, unhappy, relaxed exhausted and the like and for providing corresponding mental state data.

16. The method according to claim 1, wherein acquiring stressor data having a set of stressor data items comprises using an activity-monitoring device, including one or more sensors for automatically detecting and generating and receiving signals representing any kind of activity of the person, wherein the activity comprises at least one of sports, movement, sleeping times, times in specific situations, wherein the times comprises at least one of travel times or times talking on the phone, times in public transportation, television times, and online times.

17. The method according to claim 1, wherein acquiring stressor data having a set of stressor data items comprises using an exposure input device which is configured to query for at least one of nutrition data, medication data, drinking data, drug consumption, and exposure to UV radiation.

18. The method according to claim 1, wherein acquiring stressor data having a set of stressor data items comprises using an information exposure unit to collect information exposure data about at least one of the usage of digital media, wherein the digital media comprises at least one of social media, email communication, telephone usage, and usage of a smartphone for different kind of purposes.

19. The method according to claim 1, wherein acquiring stressor data having a set of stressor data items comprises using a voice-analyzing unit to detect the voice of the person and to analyze the voice of the person to provide voice stress data as a stressor data item depending on analyzed stress indicators.

20. The method according to claim 1, wherein acquiring stressor data having a set of stressor data items comprises using a resilience input device to query, about the physical resilience of the person.

21. A processing device for indicating a long-term stress level of a person by a computer comprising a processor and a memory, comprising:
  a receiver for receiving stressor data having a set of stressor data items;
  an artificial neural network trained for providing the stress level based on the stressor data values and an indication of previous stress state analyzing stressor data values of the stressor data items to obtain a stress level, wherein the artificial neural network is trained to provide output representing the stress level based on the stressor data values and an indication of previous stress state, wherein the artificial neural network is a recurrent neural network, wherein the indication of the previous stress state is considered via a feedback path to an input of the recurrent artificial neural network to consider the accumulating effect of stressors to which the person is exposed, wherein the artificial neural network is trained by available data of various persons who have developed a burnout syndrome, wherein the burnout syndrome defines a maximum value of a stress level, wherein missing values of one or more particular stressor data are generated by selecting relevant stressor data from the set of stressor data which have a positive correlation with the missing data above a given correlation threshold level so that a high-quality prediction of the missing stressor data can be obtained; and
  a display or an alarm configured to signal the stress level.

22. A system comprising:
  the computer according to claim 21; and
  a portable output device,
  wherein the display or alarm is configured to transmit an indication about the stress level to the portable output device so that the portable output device outputs a representation of the stress level.

* * * * *